United States Patent [19]

Gruber et al.

[11] 4,438,091

[45] * Mar. 20, 1984

[54] BROMHEXINE DELAYED-RELEASE PHARMACEUTICAL FORM

[75] Inventors: Peter Gruber, Biberach; Jochen Schmid, Warthausen; Horst Lechner; Eckhart Bauer, both of Biberach, all of Fed. Rep. of Germany

[73] Assignee: Dr. Karl Thomae GmbH, Biberach an der Riss, Fed. Rep. of Germany

[*] Notice: The portion of the term of this patent subsequent to Jan. 4, 1999 has been disclaimed.

[21] Appl. No.: 393,760

[22] Filed: Jun. 30, 1982

[30] Foreign Application Priority Data

Jul. 7, 1981 [DE] Fed. Rep. of Germany ....... 3126703

[51] Int. Cl.³ .......................... A61K 9/22; A61K 9/24
[52] U.S. Cl. ......................................... 424/21; 424/19
[58] Field of Search ................................. 424/19–22

[56] References Cited

U.S. PATENT DOCUMENTS

| | | | |
|---|---|---|---|
| 2,928,770 | 3/1960 | Bardani | 424/19 |
| 2,971,889 | 2/1961 | Swintosky | 424/31 |
| 3,247,066 | 4/1966 | Milosovich | 424/19 |
| 3,344,029 | 9/1967 | Berger | 424/19 |
| 3,538,214 | 11/1970 | Polli et al. | 424/19 |
| 3,775,537 | 11/1973 | Lehmann et al. | 424/81 |
| 3,835,221 | 9/1974 | Fulberth et al. | 424/20 |
| 3,917,813 | 11/1975 | Pedersen | 424/20 |
| 4,083,949 | 4/1978 | Benedickt | 424/19 |
| 4,361,546 | 11/1982 | Stricker et al. | 424/20 |
| 4,367,217 | 1/1983 | Gruber et al. | 424/20 |

OTHER PUBLICATIONS

Spitael et al. Pharm. Ind. 39(S): 502–505(1977) "Factors Affecting The Dissolution Rate of Enteric Coatings".

*Primary Examiner*—Shep K. Rose
*Attorney, Agent, or Firm*—Hammond & Littell, Weissenberger & Dippert

[57] ABSTRACT

This invention relates to vehicles for the administration of bromhexine. More specifically, this invention relates to a composition for the delayed release of bromhexine which comprises (i) spheroid particles or tablets comprised of (a) bromhexine and/or acid addition salts thereof and (b) at least one pharmacologically acceptable acid or acidic substance, the total amount of acid substance from acid addition salts present and the acid or acidic substance being in a ratio of at least 2 mols to 1 mol of bromhexine, and (ii) a coating surrounding said spheroid particles or tablets, said coating being comprised of from about 50 to 100 percent by weight of acid-insoluble lacquers soluble in intestinal juices and from about 0 to 50 percent by weight of lacquers insoluble in gastric and intestinal juices and said coating being present in an amount of from about 2 to 30 percent by weight, based upon the weight of the spheroid particles or tablets.

28 Claims, 1 Drawing Figure

BROMHEXINE DELAYED-RELEASE PHARMACEUTICAL FORM

FIELD OF THE INVENTION

This invention relates to vehicles for the administration of bromhexine. More specifically, this invention relates to pharmaceutical forms containing bromhexine and having a coating which acts as a dialysis membrane, the active substance being released in the gastrointestinal tract over a regulated delay period.

BACKGROUND OF THE INVENTION

The compound N-cyclohexyl-N-methyl-(2-amino-3,5-dibromobenzyl)-amine, known as bromhexine, as well as the hydrochloride thereof, comprise an active substance which has been known for many years. The therapeutic effect of bromhexine in diseases of the respiratory tract which are accompanied by a pathological change in secretion has often been confirmed by single or double blind testing. In addition to having this effect, bromhexine also affects the coughing itself. The frequency of coughing, the total number of coughing spasms, and the intensity of the cough are favorably affected. Patients always find that their breathing is eased. For this reason, a delayed-release form with a prolonged effect would be of particular benefit for patients during the night, since it would avoid the subtherapeutic levels in the blood caused by the long interval between doses of bromhexine preparations which do not have delayed release.

In addition to being useful in the treatment of annually recurring acute tracheobronchitis, bromhexine has also proven suitable for the treatment of chronic bronchitis, bronchial asthma, and chronic sinusitis, the treatment and alleviation of which require long periods of therapy. Here again, a reduction in the number of doses required per day improves patients' compliance, which, as is well-known, is particularly important in long-term medication.

In view of the obvious advantages of producing a delayed-release form of bromhexine, there has been no shortage of attempts to produce such a preparation. However, it was found that even micronized bromhexine hydrochloride introduced into the intestinal tract by means of a preparation resistant to gastric juices did not result in any appreciable absorption. In cases such as this, success is often achieved if the active substance is mixed with an emulsifier which then releases the active substance in solubilized form in the intestinal juices. However, even with this form, it has not been possible to obtain absorption from the intestines.

Generally, to develop an effective delayed-release form, an active substance must satisfy the following conditions:
(i) good pH-independent solubility in the entire gastrointestinal tract, and
(ii) no change in the speed of absorption in the absorbent part of the gastrointestinal tract.

It has been found that bromhexine does not satisfy either of these conditions. In an aqueous medium, bromhexine is soluble only in the acidic range; above a pH of 4 the substance is virtually insoluble in water. This means that bromhexine can only be dissolved and hence absorbed in the upper gastrointestinal tract, whereas, at the higher pH values which occur in the intestinal region, it remains insoluble and is not absorbed.

Since the passage time through the stomach and the upper intestinal regions (with sufficiently acid pH) is relatively short (from about 0.5 to 1 hour), it is therefore difficult to achieve absorption over several hours. Moreover, the residence period in the stomach and in the various intestinal sections can vary considerably. Thus, naturally, in the case of a substance whose solubility depends on the pH, inter-individual and intra-individual variations of levels of active substance in the blood are extremely large when the substance preparation has a slow release, as is necessary with delayed-release forms. Further, even of bromhexine is introduced in dissolved form into various intestinal sections, the absorption rate decreases sharply from the duodenum to the colon.

Normally, it is not difficult to produce delayed-release preparations with highly soluble active substances and substances which are highly soluble substantially irrespective of the pH. The delayed-release properties can be obtained, for example, by the following methods:

(1) the active substance together with excipients is formulated so that it is only released very slowly, for example, by embedding it in a matrix which dissolves extremely slowly; or (2) the active substance together with the excipients is shaped into tablets, pellets, or the like, which are then provided with a coating which results in a slow release of the active substance.

It has been found that, even if highly soluble salts of bromhexine are used, this does not result in a delayed-release form since the extreme pH dependency of the solubility of bromhexine cannot be overcome by means of acid salts alone. If, for example, bromhexine hydrochloride is made into the form of a matrix-type delayed-release tablet (Example 11), bromhexine can only be released, in dissolved form, from this preparation as long as the tablet is in the acidic medium of the stomach. When the matrix tablet reaches the small intestine, the release of active substance and hence the absorption virtually ceases. The intestinal juices momentarily buffer the acid salts to form a substantially insoluble bromhexine base. The solubility of the bromhexine base in a phosphate buffer is shown in the following table:

TABLE 1

| pH | Solubility (%) |
|---|---|
| 4.5 | 0.065 |
| 5.0 | 0.015 |
| 6.0 | 0.003 |
| 6.5 | 0.001 |
| 7.0 | 0.0003 |

Understandably, in view of these extremely low solubilities and the preliminary tests in vivo mentioned above, the development of an effective delayed-release form has seemed impossible as it presupposes that bromhexine would have to be available in dissolved and absorbable form for several hours even in the pH range of the intestinal tract.

OBJECTS OF THE INVENTION

It is an object of the invention to provide vehicles for administering bromhexine.

It is also an object of the invention to provide bromhexine-containing, delayed-release pharmaceutical forms and a method for their use.

It is a further object of the invention to provide a method of treating respiratory conditions in a host in need of such treatment which comprises administering to said host a therapeutically effective amount of a composition comprised of (i) spheroid particles comprised of (a) bromhexine and/or acid addition salts thereof and (b) at least one pharmacologically acceptable acid or acidic substance, the total amount of acid substance from acid addition salts present and the acid or acidic substance being i a ratio of at least 2 mols to 1 mol of bromhexine, and (ii) a coating surrounding said spheroid particles, said coating being comprised of from about 50 to 100 percent by weight of acid-insoluble lacquers soluble in intestinal juices and from about 0 to 50 percent by weight of lacquers insoluble in gastric and intestinal juices and said coating being present in an amount of from about 2 to 30 percent by weight, based upon the weight of the uncoated spheroid particles.

These and other objects of the invention will become more apparent in the discussion below.

DETAILED DESCRIPTION OF THE INVENTION

Applicants have developed a bromhexine delayed-release form which fully adjusts to the particular physical and biochemical properties of bromhexine and which provides a long-lasting level of bromhexine in the blood. This development has been achieved by a novel combination of different concepts and techniques concerning pharmaceutical preparations.

The following principles were applied:

(1) The insolubility of bromhexine at a higher pH value in the intestinal tract is compensated by the addition of acidifying substances.

(2) The pharmaceutical preparations obtained from bromhexine or an acid addition salt thereof and the acidifying substance are coated with a membrane which, on the one hand, has release characteristics especially suited to bromhexine, but, on the other hand, holds the acidifying substances, which normally dissolve much more rapidly, inside the pharmaceutical preparation for a sufficiently long time.

More specifically, the invention relates to spheroid particles comprised of bromhexine and/or acid addition salts thereof, which are coated with a diffusion membrane and are preferably packed into hard gelatin capsules or compressed into tablets. In addition, tablets may be prepared from bromhexine and/or acid addition salts thereof and acidifying substances, i.e., acids and/or acidic substances, by granulating these mixtures, compressing the granulate, and then coating the resulting tablets with a diffusion membrane.

The bromhexine delayed-release form of the invention preferably consists essentially of a series of spheroid particles of equal of different particle size, which are comprised of bromhexine and/or acid addition salts of bromhexine and acidifying substances, for example, organic edible acids, in a ratio of at least two moles of acidifying substance to one mole of bromhexine base, i.e., bromhexine, or one mole of acidifying substance to one mole of bromhexine salt. In other words, the total amount of acid from acid addition salt present and of acidifying substance, collectively considered the "acid substance", comprises a ratio of at least 1 mol (or acid equivalent) to 1 mol of bromhexine. The proportion of acidifying substance may also be substantially higher, for example, up to 75 mols, preferably from about 5 to 25 mols. The spheroid particles are surrounded by a diffusion membrane consisting essentially of acid-insoluble lacquers soluble in intestinal juices, the coating preferably being from about 2 to 30% by weight, preferably from about 3 to 20% by weight, based upon the weight of the uncoated spheroid particles. The ratio of bromhexine to acidifying substance must be selected so that total release of the active substance in dissolved form is ensured, irrespective of the pH medium in the gastrointestinal tract.

To produce the spheroid particles, bromhexine or acid addition salts thereof are, for example, mixed with the acid or acidic substances, for example, organic edible acids such as citric acid or tartaric acid, in accordance with the ratios specified above, and then granulated. However, the spheroid particles can also be present in the form of larger crystals with a spheroidal shape (for example, when crystallized salts of bromhexine are used), in the form of rounded granulates or in the form of small pearls or beads, that is, pellets. Such forms are produced by processes known per se. Small pellets having a diameter of from about 0.1 to 3 mm, preferably of from about 0.8 to 1.5 mm, are preferred.

Suitable acids include a plurality of toxicologically harmless, that is, pharmacologically acceptable, acids such as, for example, fumaric acid, malic acid, tartaric acid, citric acid, succinic acid, ascorbic acid, or mixtures of any of these acids while suitable acidic substances include pharmacologically acceptable acidic substances such as acid slts selected from the group consisting of, for example, sodium or potassium hydrogen sulphate, betaine hydrochloride, or the monosodium or monopotassium salts of tartaric acid or citric acid, and mixtures thereof. Starter cores for the spheroid particles can be comprised of the acids or acidic substances described above, of other pharmacologically acceptable acidifying substances, or of conventional pharmaceutically acceptable inert material such as sugar, a sugar alcohol, or the like. The acids or acidic substances in the starter core can be different from the acids or acidic substances admixed with the bromhexine. Moreover, the acid component of the mixture to be applied to the cores can consist of several of the above-mentioned acids and/or acidic substances. Especially suitable for the starter cores are those acids or acidic substances which have an approximately spherical shape, for example, tartaric acid, citric acid, malic acid, succinic acid, ascorbic acid, sodium or potassium hydrogen sulphate, monosodium or monopotassium salts of polybasic acids, betaine hydrochloride, and compounds such as succinic anhydride, which have an acid reaction after hydrolysis.

Due to the presence of spheroid particles, for example, rounded granules or pellets, the total does of active substance is divided up into many hundreds of small, individual, delayed-release forms. This ensures a statistically uniform and substantially reproducible passage of the small, delayed-release forms surrounded by diffusion membrane through the gastrointestinal tract.

As mentioned above, the particles or pellets are produced by procedures known per se, for example, by means of a tablet-coating apparatus according to the Merumeriza process, from powdered or acidifying substance and bromhexine with the aid of adhesive solutions. The preparation is also effected, for example, with the use of a pelleting plate or of wet mixing appliances with special agitator arms. However, the pellets are preferably produced by applying the active substance to starter cores which consist of suitable acids or acidic substances, in the presence of a bonding agent. Suitable bonding agents include adhesive solutions, such as starch gums, sugar syrup, and solutions of gelatin, guar gum, cellulose ethers (for example, methylcellulose, ethylcellulose, hydroxyethylcellulose, hydroxypropyl methylcellulose), or polyvinylpyrrolidone.

In a preferred preparation method, rounded starter cores of tartaric acid with an average diameter of from about 0.3 to 1 mm, preferably from about 0.6 to 0.8 mm, are sprayed uniformly with an alcoholic polyvinylpyrrolidone solution in a suitable vessel and are mixed with a mixture of 8 parts by weight of bromhexine, and 2 parts by weight of talc until the pellets, that is, the particle cores, roll freely again. After drying, this operation is repeated until the desired total amount of active substance has been applied. The bromhexine pellets obtained have a size of from about 0.7 to 0.9 mm and preferably consist of at least 90 percent by weight of active substance and acid. However, it is also possible to dissolve or suspend the active substance in the adhesive solution and to apply this solution or suspension uniformly over the surface of the starter cores.

To prepare the delayed-release tablets according to the invention, bromhexine or the salts thereof are generally mixed with the above-mentioned acidifying substances in the molar ratios described and then granulated in the moist or dry state. After screening, and possibly after the addition of further excipients, for example, magnesium stearate, the granulate is compressed to form tablets measuring, for example, from about 4 to 13 mm in diameter. The tablets thus prepared are then coated with a lacquer the composition of which will be described hereinafter.

Extensive in vitro and in vivo tests have shown that the composition of the lacquer coating is of particular importance. The lacquer sprayed onto the delayed-release forms should not dissolve in the absorbable part of the gastrointestinal tract, and the coating must remain in place in the intestinal tract until the entire amount of active substance is diffused out. The coating must retain the acid or acidic substance present in the core until the bromhexine contained therein is completely dissolved. If the coating is dissolved prematurely or breaks down, the intestinal juices, which are present in large excess, will penetrate into the delayed-release, bromhexine-containing forms and neutralize the acid or acidic substance present therein. Then, due to the virtual insolubility of bromhexine in the pH range of the intestines, no further active substance can go into solution and be absorbed. The acid or acidic substance inside the pellets, which dissolves in the fluid, dissolves the bromhexine, which is then released through the membrane of the delayed-release pellet. As a result of the increase in permeability of the coating in the intestinal tract, acidic active substance solution is increasingly released into the lower region of the intestinal tract as the pellet progresses.

The preparation procedure can also be carried out in another way whereby first the acid starter core used in the production of the granulate for the diffusion tablets or for the preparation of the pellets is sprayed with a solution of a retarding lacquer (see Example 5). This ensures that the supply of acid substance for dissolving the bromhexine is not exhausted or, if a lacquer soluble in intestinal juices is used, that the supply of acid substance increases gradually.

It was surprising and unforeseeable that bromhexine emerging from the preparation would remain absorbable in this form over a long period of time, in spite of, for example, the fact that even micronized bromhexine or bromhexine solubilized with emulsifiers and then introduced into the intestinal juices is not absorbed. The reason for this unexpected effect could be either that a supersaturated solution of bromhexine in intestinal juices is formed, which can be observed in vitro, or that the bromhexine precipitates substantially as a molecular dispersion and is then available for absorption in this finely distributed form.

In theory, the dialysis membranes of the pharmaceutical preparations of bromhexing according to the invention could consist of conventional retarding lacquers insoluble in the gastric and intestinal juices, such as ethylcellulose, acetylcellulose, or lacquer substances based on acrylate or methacrylate (available under the names Eudragit retard S ® and Eudragit retard L ® from Rohm & Haas). However, since dissolved bromhexine is absorbed particularly quickly in the uppermost section of the intestines, immediately after leaving the stomach, possibly resulting in soaring blood level peaks, and since the speed of absorption decreases significantly in the lower intestinal regions, a retard coating of this kind cannot be used to produce pharmaceutical preparations with long-lasting blood levels and a high bioavailability.

It has now been found that these disadvantages are avoided if the diffusion membrane is made from lacquers which are predominantly soluble in the intestinal juices and insoluble in the gastric juices. In this way, the release of the active substance is first delayed and then accelerated in the lower sections of the intestines. It has proven particularly advantageous to use, inter alia, a composition of about 50 percent by weight of a copolymer of methacrylic acid and methacrylic acid ester (acid number of 180 to 200), available under the name Eudragit S ®, from Rohm & Hass, and from about 50 percent by weight of hydroxypropyl methylcellulose phthalate, available under the name HP 55 ®, from Shinetsa Chem. Comp., Tokyo, both of which components are so-called lacquers soluble in intestinal juices. A solution such as, for example, a from about 10 to 15 percent solution of both components in a suitable solvent such as acetone/isopropanol (1:1) or acetone/ethanol (1:1), can be used for spraying the pharmaceutical preparations. Although such a coating consists only of components supposedly soluble in intestinal juices, the coating surprisingly does not dissolve in the absorbable part of the intestinal tract. The fact that such coatings are possible at all, and are even especially suitable in this case, is surprising for two reasons:

(1) It is stated in German Pat. Nos. 2,336,218 and 2,415,490 that at least 15 or 30 percent of the coating constituents must be insoluble in the intestinal and gastric juices, respectively, to produce a stable coating.

(2) It was not foreseeable that diffusion would occur at all, even with a lacquer which is 100% soluble in the intestinal juices, since acid is constantly being dissolved inside the pharmaceutical preparation and diffusing through the membrane.

Suitable components soluble in the intestinal juices include, in addition to those previously mentioned, the so-called gastric juice-resistant lacquers such as, for example, cellulose acetate phthalate, ethylcellulose phthalate, hydroxypropyl methylcellulose succinate, cellulose acetate succinate, hydroxypropyl methylcellulose hexahydrophthalate, cellulose acetate hexahydrophthalate, hydroxypropyl methylcellulose trimellitate, and methacrylic acid/methacrylate copolymer (acid number 300 to 330, also known as Eudragit L ®, available from Rohm & Haas), either alone or in admixture with one another.

A certain proportion of the lacquers soluble in intestinal juices can also be replaced by lacquers insoluble in both the stomach and the intestines, without the optimally acting delayed-release form thereby suffering very much in its effect. Suitable as such lacquers are ethylcellulose, as well as lacquer substances based upon acrylate or methacrylate, such as the lacquers known by the names Eudragit retard S ® and Eudragit retard L ®. The lacquer components insoluble in gastric and in intestinal juices may be present in amounts up to about 50 percent by weight, preferably up to about 30 percent by weight, or in the case of ethylcellulose, up to about 14% by weight.

To summarize, it can be said that the unusual properties of bromhexine (extremely great pH-dependency of its solubility, virtually insoluble from pH 4.0) make it necessary to use a specifically adapted type of dialysis membrane which enables the release of active substance to be controlled to some extent as a function of the pH. The composition of the coating is chosen so that, in a pH range of up to 4.0, the release of active substance is delayed and, at higher pH values, as the pH increases there is an accelerating release of active substance. The residence time of medicaments and the pH value in the stomach and in the various intestinal sections differ sharply, however, from person to person and in one and the same person at different times. Too large a pH-dependence of the release would therefore result in large differences in levels of active substance in the blood over time. However, if the total dose of bromhexine is divided into hundreds of independent, small, delayed-release forms, then a statistically uniform and substantially reproducible passage of this delayed-release form through the gastrointestinal tract is ensured. The effects of the differences in the pH gradient and the gastrointestinal motility of individual patients on the bromhexine blood level behavior are thereby largely compensated for. Thus, the implementation of the principle of controlled release dependent on the pH, in the case of bromhexine, favors the use of spheroid particles such as rounded granules or pellets rather than bi-convex tablets coated with a dialysis membrane.

The coatings or shells according to the invention may contain conventional excipients, such as plasticizers, wetting agents, or dyes. Suitable are pharmacologically acceptable plasticizers such as those selected from the group consisting of esters of phthalic acid, phorphoric acid, or citric acid, and polyethylene glycols. Preferable glyceryl tri-acetate and/or castor oil is used.

The diffusion membrane is applied to the spheroid medicament particles, that is, the pharmaceutical forms, by methods known per se. This can be effected in a rapidly rotating vessel or via the fluidized-bed process by spraying on the lacquer solution forming the diffusion membrane.

The dosage range for the active substance bromhexine is from about 5 to 100 mg, preferably from about 15 to 60 mg. The spheroid particles prepared according to the above-described processes are first provided with a diffusion membrane and are then filled into, for example, conventional hard gelatin capsules after the particles have been provided with a diffusion membrane. According to this procedure, it is possible to mix pellets or particles of different delay stages and also to optionally add undelayed active substance particles or pellets as a so-called starting dose. However, the bromhexine delayed-release particles can also be mixed with other pharmaceutical excipients and pressed into tablets. This is possible in the case of particles or pellets with a diameter below 1 mm without noticeable damage to the diffusion membrane. After such a tablet is ingested, it disintegrated in a few seconds and, like the capsules, releases the spheroid delayed-release particles of bromhexine (Example 10).

The following problems were solved by the discovery of the forms of administration of bromhexine according to the invention:

(1) It was possible to create a situation whereby bromhexine becomes soluble and independent in its solubility of the pH values of the gastrointestinal tract.

(2) A diffusion coating was developed which protects the acid or acidic substance for hours against premature buffering by the intestinal juices present in large excess. The coating ensures that all the bromhexine dissolved leaves the delayed-release pellets and that the differences in the bromhexine absorption rates in the individual sections of the gastrointestinal tract are compensated for by first a delayed release and then an accelerating release upon further penetration into the lower sections of the intestinal tract. The coating according to the invention therefore provides a pH-dependent release instead of a linear release of the active substance.

(3) Due to the division of the active substance, preferably into many hundreds of single delayed-release doses, for example, in the form of spheroid particles or pellets or rounded granulates, the effects of different residence times and of the varying pH value in the gastrointestinal tract on the blood levels of bromhexine are equalized by the statistical distribution of the rates of migration.

Figure 1:
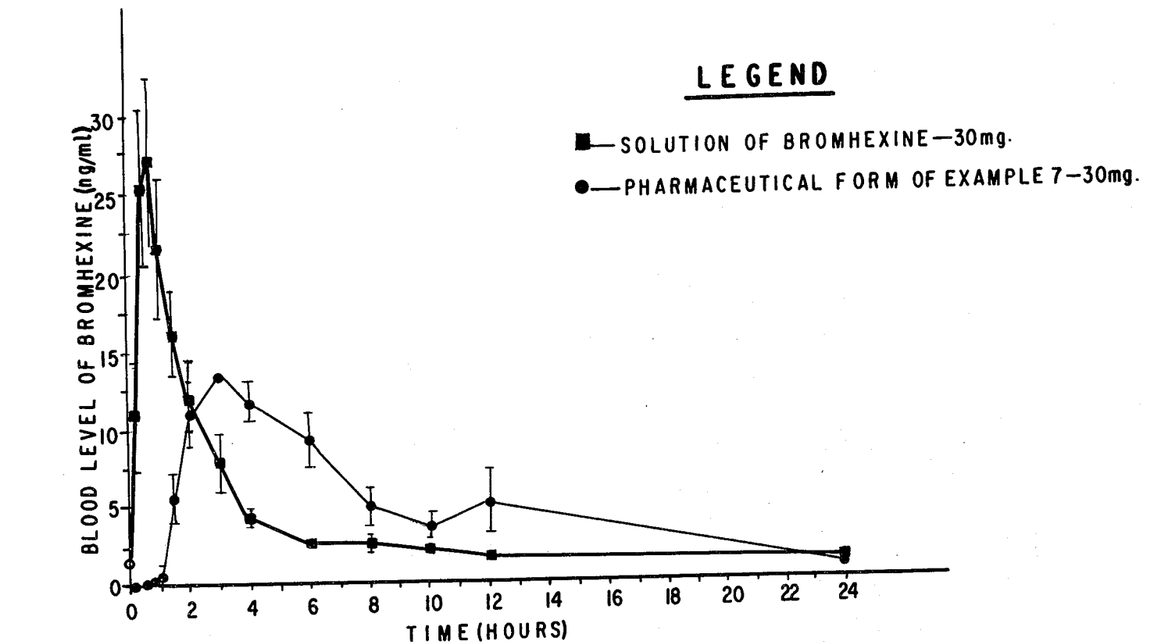
The drawing represents a comparison of the release characteristics of a bromhexine-containing solution and of an embodiment of the invention. The release characteristics are shown by blood-level curves.

The drawing shows how the blood levels of bromhexine with delayed-release forms described according to the invention differ from those obtained with a non-delayed form. As a non-delayed form, an acidic solution of bromhexine was used, whereas bromhexine pellets according to Example 7 were used as an example of a delayed-release form.

The drawing shows the mean value curves of eight test subjects. The blood level concentrations of bromhexine were determined by capillary gas chromatography after suitable processing. A comparison of the plasma levels of bromhexine after oral administration of 30 mg of bromhexine in the form of a solution and in the delayed-release pellet form shows that the delayed-release formulation delays the start of absorption by about one hour and shifts the maximum blood level from a time of about 0.75 hours (solution) to 3 hours (delayed release). The blood levels of the delayed-release form, which are to some extent significantly higher between the third and twenty-fourth hours, show that absorption from the intestines is clearly occurring over a period of many hours. Thus, for the first time, it is demonstrated that absorption can be effected by adopting suitable measures, in spite of the virtual insolubility of bromhexine in the pH range of the intestinal tract.

A comparison (x̄±Sx) of the areas under the blood level curves (AUC) provides values that are extremely unusual for delayed-release forms. The values are set forth in the following table:

TABLE 2

| Vehicle | 0–12 Hours | 0–24 Hours |
| --- | --- | --- |
| Solution | 71.6 ± 24.4 | 81.1 ± 26.4 |
| Delayed-release form of invention | 83.1 ± 19.9 | 119.4 ± 35.9 |

Thus, remarkably, the relative bioavailability of the delayed-release forms is better than that of the solution of active substance, which is normally regarded as the optimum form for absorption.

To obtain a properly functioning release of bromhexine, it is necessary to select the optimum delayed-release form, the optimum acid, the optimum quantity of acid, the optimum composition of the coating, and optimum thickness of coating. The particular difficulty is that these parameters cannot be varied independently of one another but affect one another.

The following examples are intended to illustrate the invention and should not be construed as limiting the invention thereto.

EXAMPLES

Example 1

Ten kilograms of rounded starter cores of tartaric acid with particle sizes of between 0.6 and 0.8 mm were homogeneously moistened in a rotating vessel with a 10% alcoholic polyvinylpyrrolidone solution, and then a finely powdered mixture of 8 parts by weight of bromhexine and 2 parts by weight of talc were sprinkled in until the pellets rolled freely again. After a short drying phase, further adhesive solution was sprayed in, and then more powder was added. In all, 3 kg of the powder mixture were added in this way, about 2.8 kg of adhesive solution being required. The resulting pellets of active ingredient were between 0.7 and 0.9 mm in size and contained about 18% by weight of bromhexine and 75% by weight of tartaric acid. The pellets were dried thoroughly after the last application of powder.

Example 2

Thirty kilograms of non-rounded starter cores of citric acid with particle sizes of from about 0.5 to 0.63 mm were brought to a pellet size of from about 0.8 to 1.12 mm by use of 20 kg of a powder mixture of 16 kg of bromhexine hydrochloride and 4 kg of tartaric acid, according to the procedure set forth in Example 1.

The following acids and substances of acid reaction could also be used as starter cores (in amounts of 10 kg): ascorbic acid, fumaric acid, malic acid, and succinic acid, sodium or potassium hydrogen sulphate, and monosodium or monopotassium salts of the above-mentioned polybasic organic acids. Also, the aforementioned acids and salts, as well as tartaric acid and citric acid, could be used as the acid component of the mixture to be applied, said mixture consisting of 8 parts by weight of bromhexine or bromhexine slat and 2 parts by weight of acid component. Moreover, mixtures of said acids and salts could also be used as the acid component.

The ratio by weight of the mixture of bromhexine and the acidic component which is to be applied to the cores may be 8:2, as given above, or may be one of 10:0, 9:1, 7:3, 6:4, 5:5, 4:6, 3:7, 2:8, and 1:9.

EXAMPLE 3

In a fluidized bed granulation apparatus, 10 kg of powdered bromhexine were mixed with 22 kg of powdered fumaric acid. A compound granulate was prepared by slow spraying with 25 kg of a 5% hydroxypropyl methylcellulose solution (methylene chloride/isopropanol). Ninety percent of the dried, spherical granulate was between 0.6 and 1.0 mm in diameter. The bromhexine content was about 30% by weight.

In place of fumaric acid, it is also possible to use citric acid, ascorbic acid, tartaric acid, malic acid, succinic acid, a monosodium or monopotassium salt of the above mentioned polybasic acids, or sodium or potassium hydrogen sulphate.

The bromhexine content by weight may also be adjusted to one of the values 5%, 10%, 20%, 40%, and 50% by alteration of the composition of the mixture.

EXAMPLE 4

Fifteen kilograms of sugar pellets with diameters of from about 0.6 to 0.8 mm were homogeneously moistened in a rotating vessel with a 5% alcoholic hydroxypropyl cellulose solution, and then a finely powdered mixture of 7 kg of bromhexine citrate, 2 kg of fumaric acid, and 1 kg of talc was sprinkled in until the pellets rolled freely again. After drying and wetting, further powder was added. To apply all the powder, about 12 kg of adhesive solution were required. After thorough drying and screening, the pellets of bromhexine active substance were coated with a 1% by weight protective film of hydroxypropyl methylcellulose.

EXAMPLE 5

Ten kilograms of rounded starter cores of tartaric acid with particle sizes of from about 0.6 to 0.8 mm were sprayed in a rotating vessel with a 12.5% alcoholic solution of a methacrylic acid/methacrylic acid ester copolymer (Eudragit S ®). A total of 1.5% by weight of dry lacquer substance was applied. The coated pellets of tartaric acid were coated with bromhexine and talc in accordance with the procedure set forth in Example 1. Enough powder was added to give a content of active substance of 12% by weight.

EXAMPLE 6

Fifteen kilograms of bromhexine hydrochloride, 55 kg of fumaric acid, and 9 kg of polyvinyl pyrrolidone were mixed in a cube mixer for 20 minutes. An amount of 0.4 kg of magnesium stearate was added, and after mixing continued for a short time, the powder was added via a roller compactor to which a dry granulation apparatus with screening means was connected. The fraction having particle sizes from about 0.63 to 1.0 mm was used. Any finer constituents were recycled to be compressed and broken up again. The fraction screened off was rounded off in a fluidized bed apparatus by spraying with a dilute talc paste and then with a 10% lacquer solution consisting of 8 parts of methacrylic acid/methacrylic acid ester copolymer (Eudragit S ®) and 2 parts of a copolymer of acrylic and methacrylic acid esters (Eudragit retard S ®) in isopropanol/acetone (7:3). Relative to the granulate, 8% by weight of lacquer and 1% by weight of polyethylene glycol 6000 were sprayed on as the plasticizer.

The in vitro release of the active substance bromhexine was tested under the following conditions:

USP XX-paddle method, 100 revolutions per minute at 37° C.
1st hour: pH 1.2 (USP gastric juice)
2nd to 8th hours: pH 5.5 (phosphate buffer)
The results are set forth in the following table:

TABLE 3

| Hour | Release of Active Substance (% by weight) |
|---|---|
| 1 | 25 |
| 2 | 44 |
| 3 | 59 |
| 4 | 71 |
| 5 | 80 |
| 6 | 87 |
| 7 | 93 |
| 8 | 98 |

EXAMPLE 7

Nineteen kilograms of pellets of the active ingredient bromhexine produced according to Example 1 were sprayed, in a rapidly rotating tablet-coating vessel provided with baffle plates, with a solution of
methacrylic acid/methacrylic acid ester copolymer (Eudragit S ®): 900 gm
hydroxypropyl methylcellulose phthalate (HP 55 ®): 900 gm
in 16.2 kg of isopropanol/acetone (7:3). One hundred eighty grams of triacetin were added as plasticizer.

After drying, the in vitro release of bromhexine was measured using the procedure set forth in Example 6. The results were as follows:

TABLE 4

| Hour | Release of Active Substance (% by weight) |
|---|---|
| 1 | 12.5 |
| 2 | 36.2 |
| 3 | 59.6 |
| 4 | 69.5 |
| 5 | 79.0 |
| 6 | 88.1 |
| 7 | 94.4 |

It can be seen that a significant acceleration of release occurred in the second and third hours.

In analogous manner, pellets prepared according to Examples 1, 2, and 4, were sprayed with the following compositions:
(a) Copolymer of acrylic acid and methacrylic acid esters (Eudragit retard S ®): 30 parts
Methacrylic acid/methacrylic acid ester copolymer (Eudragit S ®): 60 parts
Polyethyleneglycol 6000: 10 parts
(b) Cellulose acetate phthalate: 30 parts
Hydroxypropyl methylcellulose phthalate (HP 55 ®): 60 parts
Triacetin: 10 parts
(c) Ethylcellulose phthalate: 70 parts
Copolymer of acrylic acid and methacrylic acid ester (Eudragit retard S ®): 20 parts
Triacetin: 10 parts
(d) Ethylcellulose: 10 parts
Hydroxypropyl methylcellulose succinate: 80 parts
Triacetin: 10 parts

EXAMPLE 8

Twelve kilograms of pellets of the active substance bromhexine prepared according to Example 5 were sprayed, in a rapidly rotating coating vessel with baffle plates, with a solution of 720 gm of methacrylic acid/methacrylic acid ester copolymer (Eudragit S ®) in 6.48 kg of isopropanol.

After drying, the in vitro release of bromhexine was measured using the procedure set forth in Example 6. The results were as follows:

TABLE 5

| Hour | Release of Active Substance (% by weight) |
|---|---|
| 1 | 3.2 |
| 2 | 14.5 |
| 3 | 35.1 |
| 4 | 58.0 |
| 5 | 74.8 |
| 6 | 85.3 |
| 7 | 94.1 |
| 8 | 100.0 |

As a result of the insulation of the starter core of tartaric acid, accelerated release did not begin to occur until the third hour with the delayed-release pellets. Pellets of this kind are particularly suitable for mixing with starter pellets not having delayed release characteristics.

EXAMPLE 9

Granules prepared according to Example 3 were mixed with 0.3% by weight of magnesium stearate and compressed to form biconvex tablet cores measuring 6 mm in diameter and weighting 100 mg. Five kilograms of these cores were sprayed, in a coating vessel, with a 10% solution (acetone/isopropanol) of
copolymer of acrylic acid and methacrylic acid esters (Eudragit retard S ®): 25 parts
hydroxypropyl methylcellulose phthalate (HP 55 ®): 65 parts
triacetin: 10 parts
The resulting dry coating comprised 6.5% by weight.

The in vitro release of bromhexine was measured using the procedure set forth in Example 6. The results were as follows:

TABLE 6

| Hour | Release of Active Substance (% by weight) |
|---|---|
| 1 | 15.5 |
| 2 | 35.3 |
| 3 | 57.8 |
| 4 | 70.0 |
| 5 | 78.7 |
| 6 | 85.3 |
| 7 | 89.2 |
| 8 | 93.4 |

Although these release levels are virtually identical to the values obtained with pellets prepared according to Example 7, in vivo testing of these delayed-release tablets showed greater fluctuations in the blood levels of bromhexine and a relative bioavailability which was about 25% lower than that obtained with the pellets.

EXAMPLE 10

Two kilograms of coated bromhexine pellets prepared according to Example 6 were mixed with 1.5 kg of microcrystalline cellulose, 0.4 kg of corn starch, and 0.1 kg of polyvinylpyrrolidone. After the addition of 20 gm of magnesium stearate, mixing was continued for a further five minutes. Tablets were compressed from the mixture, gentle pressure being used. The tablets disintegrated in about 45 seconds; the release of bromhexine from the individual delayed-release pellets accelerated only slightly.

EXAMPLE 11

Quantities of 1.5 kg of bromhexine hydrochloride, 1.0 kg of lactose, 0.5 kg of polyvinylpyrrolidone, and 6.9 kg of polyacrylic acid (available under the name Carbopol 940 ® from B. F. Goodrich Chemical Co.) were moistened with alcohol and granulated through a screen with a mesh size of 1.5 mm. After drying, 0.1 kg of magnesium stearate was added, and the granules were compressed to form 9 mm matrix tablets weighing 200 mg. By use of the procedure set forth in Example 6, the in vitro release of bromhexine was measured, and the results are set forth in the following table:

TABLE 7

| Hour | Release of Active Substance (% by weight) |
|---|---|
| 1 | 26.2 |
| 2 | 29.7 |
| 3 | 30.9 |
| 4 | 32.1 |
| 8 | 37.3 |

The preceding specific embodiments are illustrative of the practice of the invention. It is to be understood, however, that other excipients known to those skilled in the art or disclosed herein, may be employed without departing from the spirit of the invention or the scope of the appended claims.

We claim:

1. A composition for the delayed release of bromhexine which comprises (i) spheroid particles or tablets comprised of (a) bromhexine and/or acid addition salts thereof and (b) at least one pharmacologically acceptable acid or acidic substance, the total amount of acid substance from acid addition salts present and the acid or acidic substance being in a ratio of at least 2 mols to 1 mol of bromhexine, and (ii) a coating surrounding said spheroid particles or tablets, said coating being comprised of from about 50 to 100 percent by weight of lacquers insoluble in gastric juices and soluble in intestinal juices and from about 0 to 50 percent by weight of lacquers insoluble in gastric and intestinal juices and said coating being present in an amount of from about 2 to 30 percent by weight, based upon the weight of the spheroid particles or tablets.

2. The composition of claim 1, wherein there are up to 75 mols of acid or acidic substance per mol of bromhexine or acid addition salt thereof.

3. The composition of claim 1, wherein the spheroid particles or tablets comprise bromhexine as component (a) and the acid or acidic substance is present in a ratio of at least 2 mols to 1 mol of bromhexine.

4. The composition of claim 1, wherein the spheroid particles or tablets comprise acid addition salts of bromhexine as component (a) and the acid or acidic substance is present in a ratio of at least 1 mol to 1 mol of acid addition salts of bromhexine.

5. The composition of claim 1, wherein the coating is present in an amount of from about 3 to 20 percent by weight.

6. The composition of claim 1 which comprises spheroid particles comprising rounded granules or pellets and having a diameter of from about 0.1 to 3 mm.

7. The composition of claim 6, wherein the diameter is from about 0.8 to 1.5 mm.

8. The composition of claim 1 which comprises tablets having a diameter of from about 4 to 13 mm.

9. The composition of claim 1, wherein the acid is selected from the group consisting of fumaric acid and tartaric acid.

10. The composition of claim 1, wherein the coating comprises from 0 to about 14 percent by weight of ethylcellulose.

11. The composition of claim 1, wherein the coating contains lacquers insoluble in gastric and intestinal juices.

12. The composition of claim 1, wherein the lacquers insoluble in gastric and intestinal juices comprise copolymers of acrylic acid and methacrylic acid esters.

13. The composition of claim 1, wherein the lacquers insoluble in gastric juices and soluble in intestinal juices are selected from the group consisting of methacrylic acid/methacrylate copolymers (acid number 180 to 200), hydroxypropyl methylcellulose phthalate, cellulose acetate phthalate, ethylcellulose phthalate, hydroxypropyl methylcellulose succinate, cellulose acetate succinate, hydroxypropyl methylcellulose hexahydrophthalate, cellulose acetate hexahydrophthalate, hydroxypropyl methylcellulose trimellitate, methacrylic acid/methacrylate copolymer (acid number 300 to 330), and mixtures of one or more thereof.

14. The composition of claim 13, wherein said lacquers comprise from about 50 to 90 percent by weight of methacrylic acid methacrylate copolymer (acid number 180 to 200) and of from about 10 to 50 percent by weight of hydroxypropyl methylcellulose phthalate.

15. The composition of claim 14, wherein said lacquers comprise about 50 percent by weight of methacrylic acid/methacrylate copolymer (acid number 180 to 200) and about 50 percent by weight of hydroxypropyl methylcellulose phthalate.

16. The composition of claim 14 which contains an additional outer coating comprising a lacquer soluble in intestinal juices.

17. The composition of claim 1, wherein the spheroid particles comprise cores consisting essentially of acid or acidic substance and having a lacquer component soluble in intestinal juices, to which bromhexine or acid addition salts are applied.

18. The composition of claim 1, wherein coated spheroid particles are contained in conventional hard gelatin capsules.

19. The composition of claim 1, wherein the coated spheroid particles have diameters of up to 1.5 mm and are contained with conventional excipients in tablet form.

20. The composition of claim 1, wherein the spheroid particles have cores comprised of an acid or acidic substance different from the acid or acidic substance in admixture with bromhexine.

21. The composition of claim 1, wherein the lacquer insoluble in gastric juices and soluble in intestinal juices is soluble at a pH of about 4.5 or greater.

22. The composition of claim 1, wherein the coating is comprised of 100 percent by weight of lacquers insoluble in gastric juices and soluble in intestinal juices.

23. A hard gelatin capsule which contains an effective amount of a composition of claim 1, wherein the bromhexine and/or acid addition salts thereof are present in an amount of from about 5 to 100 mg.

24. The capsule of claim 23, wherein the bromohexine and/or acid addition salts thereof are present in an amount of from about 15 to 60 mg.

25. A tablet which comprises a compressed mixture of an effective amount of a composition of claim 1, wherein the coated spheroid particles thereof have a particle size of up to 1.5 mm and conventional pharmaceutical excipients and wherein the bromhexine and/or acid addition salts thereof are present in an amount of from about 5 to 100 mg.

26. The tablet of claim 25, wherein the bromhexine and/or acid addition salts thereof are present in an amount of from about 15 to 60 mg.

27. A method for the treatment of respiratory disorders in a host in need of such treatment which comprises administering to said host a therapeutically effective amount of a composition of claim 1.

28. A process for the preparation of a delayed-release bromhexine composition of claim 1 which comprises the steps of:

(a) uniformly spraying rounded starter cores having an average diameter of from about 0.3 to 1 mm with an alcoholic polyvinyl pyrrolidone solution;

(b) mixing the sprayed starter cores from step (a) with a mixture of bromhexine and/or acid addition salts thereof and a sufficient amount of acidifying substance to make the bromhexine component water-soluble until the starter cores thus treated roll freely;

(c) drying the treated cores from step (b), steps (a) to (c) being repeated until the treated cores obtain a size of from about 0.1 to 3 mm; and (d) applying to the treated cores from step (c) a lacquer coating comprising from about 50 to 100 percent by weight of pharmacologically acceptable lacquers insoluble in gastric juices and soluble in intestinal juices and from 0 to about 50 percent by weight of pharmacologically acceptable lacquers insoluble in gastric and intestinal juices, said coating being present in an amount of from about 2 to 30 percent by weight, based on the weight of the spheroid particles.

* * * * *

UNITED STATES PATENT AND TRADEMARK OFFICE
CERTIFICATE OF CORRECTION

PATENT NO. : 4,438,091

DATED : March 20, 1984

INVENTOR(S) : PETER GRUBER et al.

It is certified that error appears in the above-identified patent and that said Letters Patent is hereby corrected as shown below:

Column 3, line 10, "i" should read -- in --.

Column 9, line 1, "$(x \pm Sx)$" should read -- $(\bar{x} \pm \bar{S}\bar{x})$ --.

Column 9, line 62, "slat" should read -- salt --.

Column 12, line 30, "weighting" should read -- weighing --.

Signed and Sealed this

First Day of January 1985

[SEAL]

Attest:

*Attesting Officer*

GERALD J. MOSSINGHOFF

*Commissioner of Patents and Trademarks*

UNITED STATES PATENT AND TRADEMARK OFFICE
CERTIFICATE OF CORRECTION

PATENT NO. : 4,438,091

DATED : March 20, 1984

INVENTOR(S) : PETER GRUBER et al.

It is certified that error appears in the above-identified patent and that said Letters Patent is hereby corrected as shown below:

Title page, left-hand column, the "Notice:" should read

— The portion of the term of this patent subsequent to Jan. 4, 2000 has been disclaimed. —

*Signed and Sealed this*

*Second* Day of *July 1985*

[SEAL]

*Attest:*

DONALD J. QUIGG

*Attesting Officer*     *Acting Commissioner of Patents and Trademarks*